(12) United States Patent
Marcus et al.

(10) Patent No.: US 11,344,239 B2
(45) Date of Patent: May 31, 2022

(54) NON-INVASIVE SYSTEM AND METHOD OF SPATIAL LOCALIZATION OF SPECIFIC ELECTROCARDIAC ELEMENTS

(71) Applicant: Medicomp, Inc., Melbourne, FL (US)

(72) Inventors: Sean Marcus, Rockledge, FL (US); Anthony Balda, Satellite Beach, FL (US); Scott Baskerville, Melbourne, FL (US); George Koos, Melbourne Beach, FL (US)

(73) Assignee: Medicomp, Inc., Melbourne, FL (US)

( * ) Notice: Subject to any disclaimer, the term of this patent is extended or adjusted under 35 U.S.C. 154(b) by 46 days.

(21) Appl. No.: 16/508,646

(22) Filed: Jul. 11, 2019

(65) Prior Publication Data
US 2019/0328263 A1    Oct. 31, 2019

Related U.S. Application Data

(63) Continuation-in-part of application No. 15/835,561, filed on Dec. 8, 2017, now Pat. No. 10,772,523.
(Continued)

(51) Int. Cl.
*A61B 5/282*     (2021.01)
*A61B 5/053*     (2021.01)
(Continued)

(52) U.S. Cl.
CPC ............. *A61B 5/282* (2021.01); *A61B 5/053* (2013.01); *A61B 5/361* (2021.01); *A61B 5/6832* (2013.01);
(Continued)

(58) Field of Classification Search
CPC ...... A61B 2562/046; A61B 2560/0412; A61B 5/6823; A61B 5/062; A61B 5/061; A61B 5/064; A61B 5/065; A61B 5/6833; A61B 5/6832; A61B 5/0515; A61B 5/0522; A61B 5/0531; A61B 5/053; A61B 5/046; A61B 5/042; A61B 5/04087; A61B 5/04085; A61B 5/361; A61B 5/282;
(Continued)

(56) References Cited

U.S. PATENT DOCUMENTS 6,185,448 B1 * 2/2001 Borovsky ................ A61B 5/06
                                                   600/424
2002/0188174 A1 * 12/2002 Aizawa ................. A61B 5/064
                                                   600/118
(Continued)

OTHER PUBLICATIONS

U.S. Appl. No. 15/835,561, filed Dec. 8, 2017.
USPTO Office action in related U.S. Appl. No. 15/835,561 dated Jan. 7, 2020; 30 pages.

*Primary Examiner* — Matthew Kremer
*Assistant Examiner* — Avery M Foley
(74) *Attorney, Agent, or Firm* — Kelly G. Swartz; Widerman Malek, PL (57) ABSTRACT

A patch includes a sensor layer and adhesive disposed along an outer surface of the sensor layer. The sensor layer has a plurality of sensors, each adapted to measure a value of an electric field, and a plurality of magnets wherein each of the plurality of magnets is collocated with one of the plurality of sensors. Electric field data from the plurality of sensors is provided to a cardiac monitor.

8 Claims, 5 Drawing Sheets

Related U.S. Application Data which is a continuation-in-part of application No. PCT/US2016/036478, filed on Jun. 8, 2016.

(60) Provisional application No. 62/172,565, filed on Jun. 8, 2015.

(51) Int. Cl.
  *A61B 5/00* (2006.01)
  *A61B 90/00* (2016.01)
  *A61B 5/361* (2021.01)
  *A61B 5/06* (2006.01)
  *A61B 17/00* (2006.01)

(52) U.S. Cl.
  CPC .............. *A61B 90/36* (2016.02); *A61B 90/39* (2016.02); *A61B 5/065* (2013.01); *A61B 5/6823* (2013.01); *A61B 2090/363* (2016.02); *A61B 2090/3929* (2016.02); *A61B 2090/3954* (2016.02); *A61B 2090/3966* (2016.02); *A61B 2560/0412* (2013.01); *A61B 2562/046* (2013.01)

(58) Field of Classification Search
  CPC .... A61B 2090/3966; A61B 2090/3958; A61B 2090/3954; A61B 2090/3941; A61B 2090/3937; A61B 2090/3929; A61B 2090/363; A61B 90/39; A61B 90/36; A61B 2090/3925; A61B 2017/00876
  See application file for complete search history.

(56) References Cited

U.S. PATENT DOCUMENTS

| | | | |
|---|---|---|---|
| 2006/0085049 A1 | 4/2006 | Cory et al. | |
| 2008/0200802 A1* | 8/2008 | Bhavaraju | A61B 5/05 600/426 |
| 2010/0249860 A1* | 9/2010 | Shuros | A61N 1/3625 607/4 |
| 2014/0074076 A1 | 3/2014 | Gertner | |
| 2014/0200430 A1* | 7/2014 | Spector | A61B 5/287 600/374 |
| 2015/0216438 A1* | 8/2015 | Bokan | A61B 5/044 600/515 |
| 2015/0320515 A1* | 11/2015 | Edwards | A61B 8/4254 600/389 |
| 2015/0351690 A1* | 12/2015 | Toth | A61B 5/6839 600/373 |
| 2016/0287116 A1* | 10/2016 | He | A61B 6/503 |

* cited by examiner

NON-INVASIVE SYSTEM AND METHOD OF SPATIAL LOCALIZATION OF SPECIFIC ELECTROCARDIAC ELEMENTS

RELATED APPLICATIONS

This is a continuation-in-part of U.S. Patent Application Publication No. 2018/0110436 titled Non-Invasive System and Method of Spatial Localization of Specific Electrocardiac Elements, with a filing date of Dec. 8, 2017, which, in turn, is a continuation-in-part of International Application PCT/US16/36478 titled Non-Invasive System and Method of Spatial Localization of Specific Electrocardiac Elements, with an international filing date of Jun. 8, 2016, which claims the benefit under 35 U.S.C. § 119(e) of U.S. Provisional Patent Application Ser. No. 62/172,565 titled Non-Invasive System and Method of Spatial Localization of Specific Electrocardiac Elements filed Jun. 8, 2015, the entire contents of which are incorporated herein by reference.

FIELD OF THE INVENTION

The present invention relates to the field of atrial ablation and, more specifically, to systems and methods for locating and ablating foci of arrhythmia.

BACKGROUND

Much work is being done to develop a system which is capable of accurately locating arrhythmogenic foci within the electrical system of the heart. Existing systems with the purpose of mapping the electrical potential distribution throughout the cardiac system maintain relatively low resolutions, and are unable to provide any clinically significant data. Currently, invasive catheter-based systems are used to locate these problematic cardiac foci, which cause arrhythmias like atrial fibrillation. The existing catheter procedures are generally done as a prelude to ablation after the faulty components within the hearts chambers have been located and identified.

While some research has been done in the area of using anatomic imaging methods like CT and MRI in conjunction with external or superficial body surface potential mapping to correlate both cardiac anatomy and electrophysiology, a significant problem facing the development of a device with functionality worthy of a clinical setting lies within the mathematical principles of reconstructing an electromagnetic field source using collected field data after it has been subject to a volume conductor (the human body). Due to the nature of the problem, many different valid mathematical solutions can be reached using the same field data. This leads to the inability of a system to accurately describe the source(s) which produced the resulting field experienced by the sensor arrays. The following proposed system looks to address these issues.

SUMMARY OF THE INVENTION

With the above in mind, embodiments of the present invention are related to a patch having a sensor layer and adhesive disposed along an outer surface of the sensor layer. The sensor layer may have a plurality of sensors, each adapted to measure a value of an electric field, and a plurality of magnets wherein each of the plurality of magnets is collocated with one of the plurality of sensors. Electric field data from the plurality of sensors may be provided to a cardiac monitor.

The sensor layer may be adapted to adhere to a patient and wrap from an anterior to a posterial aspect of a torso of the patient.

The plurality of magnets may be configured to form a lattice of detection.

The patch may also include a fiducial layer having a surface adapted to secure to the sensor layer. The fiducial layer further include a plurality of fiducial markers having at least one of acoustic properties, material density, and proton content different from those of human tissue.

The patch may have an electrode layer having at least one electrode and secured to the sensor layer and a cardiac monitor in electrical communication with the at least one electrode. The cardiac monitor may be adapted to identify atrial fibrillation in data provided by the at least one electrode.

The cardiac monitor may provide electric field data corresponding in time to the detection of atrial fibrillation to an external computing device adapted to locate one or more foci causing the atrial fibrillation.

The patch may include a sensor layer, adhesive, a fiducial layer, and an electrode layer. The sensor layer may include a plurality of sensors, each adapted to measure a value of an electric field, and a plurality of magnets, wherein each of the plurality of magnets is collocated with one of the plurality of sensors. The adhesive may be disposed along an outer surface of the sensor layer. The fiducial layer may have a surface adapted to secure to the sensor layer. The electrode layer may have at least one electrode and be secured to the sensor layer. Electric field data from the plurality of sensors may be provided to a cardiac monitor. The sensor layer may be adapted to adhere to a patient and wrap from an anterior to a posterial aspect of a torso of the patient. The plurality of magnets may be configured to form a lattice of detection. The fiducial layer may include a plurality of fiducial markers having at least one of acoustic properties, material density, and proton content different from those of human tissue. The cardiac monitor may be in electrical communication with the at least one electrode. The cardiac monitor may be adapted to identify atrial fibrillation in data provided by the at least one electrode. The cardiac monitor may provide electric field data corresponding in time to the detection of atrial fibrillation to an external computing device adapted to locate one or more foci causing the atrial fibrillation.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text provides apparatus, systems, and methods that may introduce additional mathematical constraints on available mathematic solutions to create an electromagnetic field map of a patient. The constrained solutions used to create an electromagnetic field map may combine anatomic imaging methods, by way of example and not as a limitation, such as CT, MRI, or the like, in conjunction with external or superficial body surface potential mapping. The use of anatomic imaging, body surface potential mapping, or both may be used to correlate cardiac anatomy with electrophysiology. Additionally, relevant probabilistic evaluation techniques may be incorporated to weigh, compare, or otherwise determine the viability of those possible mathematic solutions that remain viable.

The inventive system may comprise several parts that may work together with a common goal of non-invasive spatial location of arrhythmogenic foci. Through the implementation of different detection devices, a variety of independent data types may be analyzed and co-referenced to enhance the mathematical ability of the system to isolate the location of likely sources of arrhythmia, etc.

Figure 2:
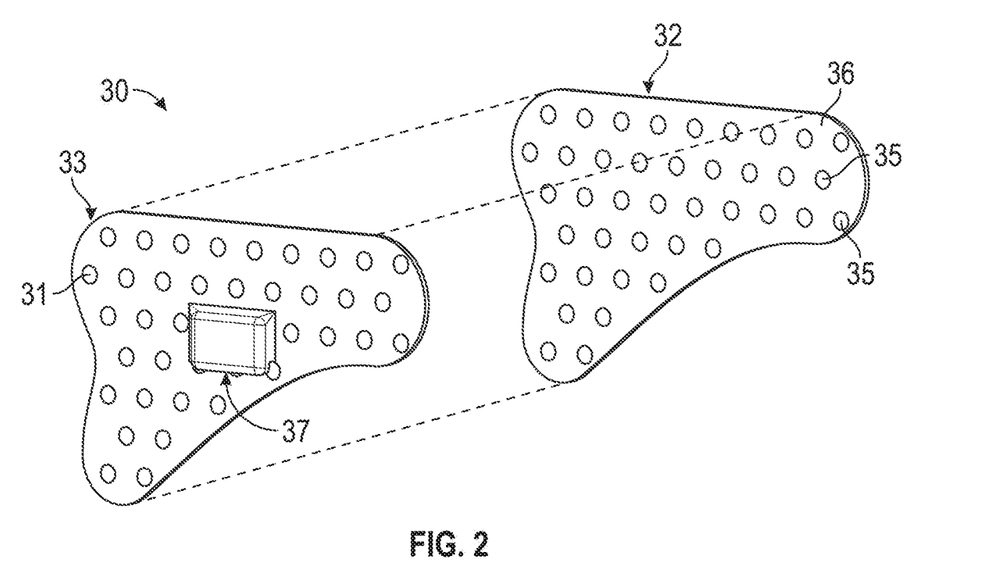
FIG. 2 is an exploded perspective view of the sensing patch illustrated in FIG. 1.

Referring initially to FIG. 2, an exploded view of an embodiment of the sensing patch 30 according to the present invention is depicted. The sensing patch 30 may include a plurality of layers. In one embodiment, the sensing patch 30 may have a sensor layer 33, a fiducial layer 32, a control layer 37, and a protective layer. Other embodiments may have a control layer 37 incorporated into or disbursed throughout a sensor layer 33. Any combination of these layers is possible within the scope of this invention.

Figure 7:
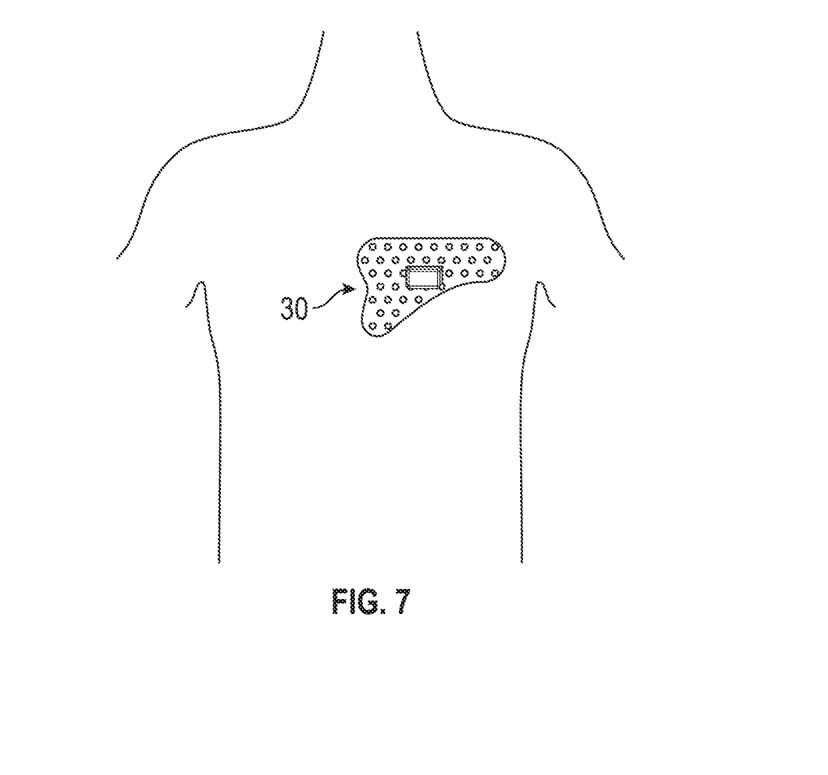
FIG. 7 is an environmental view of the sensing patch illustrated in FIG. 1 affixed to a patient.

As perhaps best illustrated in FIG. 7, the sensing patch 30 may be affixed to a patient's skin. Returning to FIG. 2, the fiducial layer 32 may be proximate to the patient's skin. The fiducial layer 32 may have biocompatible adhesives disposed along the surface contacting the patient's skin. The biocompatible adhesive may be used to secure the sensing patch 30 to the patient's skin. The fiducial layer 32 may firmly attach to a patient's skin on one side and be removably secured to the sensor layer 33 on the other side. In other embodiments, the fiducial layer 32 may firmly attach to a patient's skin on one side and be surrounded by, surround, border, or otherwise be proximate to the sensor layer 33. The fiducial layer 32 may include fiducial markers 35 disposed on a fiducial layer surface 36. The fiducial markers 35 may be compatible with imaging systems, such as, but not limited to, magnetic resonance imaging (MRI), ultrasound (US), and x-ray computed tomography (CT), and remain affixed to a patient while MRI, US, or CT imaging is performed.

In embodiments intended for use with US imaging, the material used to create the fiducial markers 35 may be any material that has acoustic properties different from those of human tissue. The greater the difference, the more the signal from the fiducial markers 35 will be evident. In embodiments intended for use with imaging systems other than US imaging, the fiducial marker 35 material density or proton content may provide the properties necessary to differentiate the fiducial markers 35 from the native tissue. The fiducial markers 35 may be plastic, metal, or the like. However, for a system compatible with all imaging modalities, including MRI, it may be desirable to utilize a non-magnetic material.

The fiducial markers 35 may be configured in an array such that the image of the fiducial markers 35 allows the system to identify where the imaging device is placed and how it is oriented at any given time. Specifically, when the fiducial markers 35 are imaged using US technology, the arrangement of the fiducial markers 35, or their appearance in a US image, may allow the system to determine the location and orientation of the US wand. This orientation may either be directly detected or interpreted by the US system or may be derived from the signal data obtained from the sensing patch 30 or imaging device, including the US wand itself. The fiducial layer 32 may comprise an array of a plurality of unique fiducials, a dual-axis barcode system, a tri-axis barcode system, or the like. The dual-axis barcode system may be a 2-dimensional (M×N) matrix or arrangement of fiducial markers 35. The fiducial markers 35 may be oriented in such a way that for any given probe location the US system is able to extract fiducial data at that point and correlate that data with a spatial location on the patch. For this barcode system, there may be multiple strips of fiducial markers 35 arranged in rows. Each fiducial marker 35 that makes up one of these rows may have a unique width. There may also be multiple strips of fiducial markers 35 arranged in columns orthogonal to the rows. Each fiducial marker 35 that makes up one of these columns may have a unique width. The US system may identify the unique width associated with a given row and the unique width associated with a given column at locations where the rows and columns intersect. The US system may then be able to correlate those two measurements with a specific point on the sensing patch 30. This dual-axis-type barcode system may be most efficient with the US probe oriented at a 90° angle in relation to the surface of the sensing patch 30.

In embodiments utilizing a third axis, a tri-axis barcode system, the fiducial markers 35 may be arranged in a 3-dimensional (M×N×P) matrix. Such an arrangement may provide the system with more data to determine the current angle of the probe and allow for more accurate and flexible image reconstruction. For this tri-axis barcode system, fiducial markers 35 may be arranged as rows, with each fiducial marker 35 in the row having a unique width, fiducial markers 35 may be arranged as columns orthogonal to the rows, with each fiducial marker 35 in the column having a unique width. The US system may identify the unique width associated with a given row and the unique width associated with a given column. The fiducial markers 35 arranged in the third dimension may all be of uniform dimensions. The US system may then be able to correlate those three measurements with a specific point on the sensing patch 30.

Figure 8:
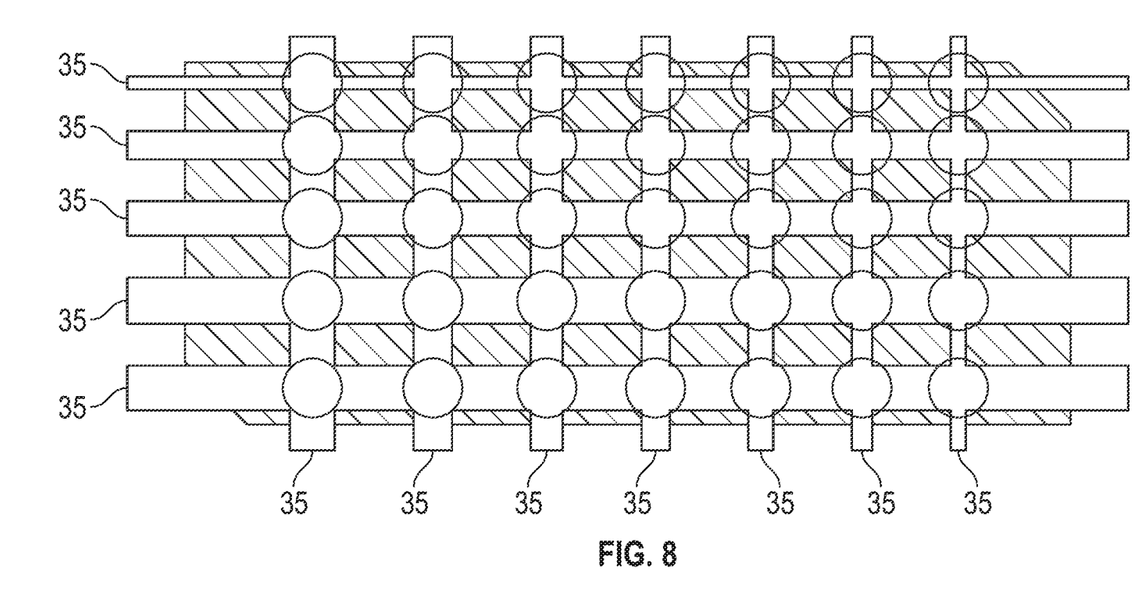
FIG. 8 is a perspective view of an array of fiducial markers to be used in connection with the sensing patch according to an embodiment of the present invention.

FIG. 8 depicts an exemplary dual-axis barcode system. The black bars depict the fiducial markers 35 and the white circles indicate the identifiable points. For the tri-axis fiducial matrix, an additional set of fiducials markers 35, similar to those shown in FIG. 8 may be arranged at another point along the layer axis. The fiducial markers 35 in the additional set of fiducial markers may be of uniform dimensions. Such a configuration may provide the system with a reference for the angle of US probe.

The unique widths of the fiducial markers 35 used in rows may be different from the set of unique widths of the fiducial markers 35 used in columns. This may assist in orienting the system and provide a reference for horizontal versus vertical direction.

The fiducial markers 35 may be of a uniform size and distribution. Such a configuration may allow for simple trigonometric calculations to be used to determine probe angle. The fiducial markers 35 may also be within the same plane and be made of a material with easily differentiable acoustic impedances so as not to be confused with other materials.

Figure 5:
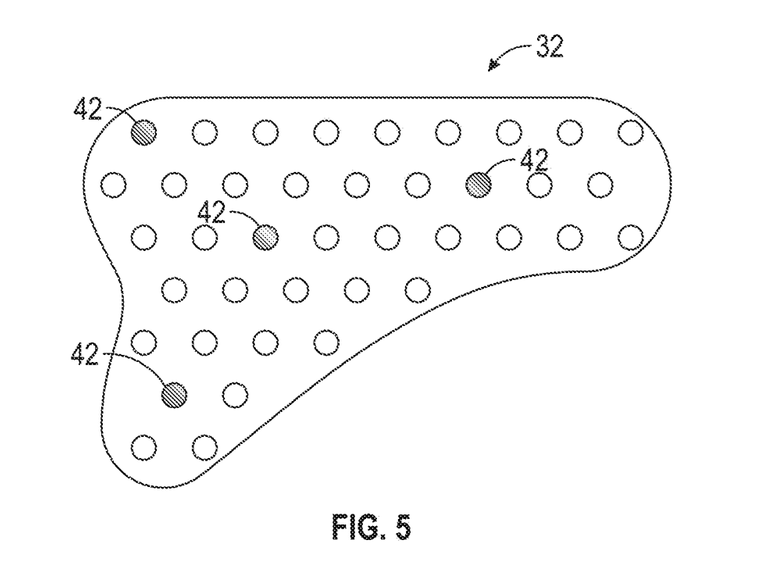
FIG. 5 is a top plan view of a fiducial layer of the sensing patch illustrated in FIG. 1.

FIG. 5 depicts a top view of the fiducial layer 32. Conductive areas 42 may be disposed on the fiducial layer 32. The conductive areas 42 may be openings, apertures, isolated conductive substances, by way of example, but not as a limitation, Ag/AgCl gel, or the like. The conductive areas 42 may correlate spatially with contact points of the sensor layer. The fiducial layer 32 may consist primarily of a material that has poor conductivity so as not to diminish the measurable electrical potential signals across each sensor contact point. However, the conductive areas 42 of the fiducial layer 32 correlating to the contact points on the sensor layer may have high conductivity. The fiducial layer 32 may also be made from materials that are compatible with the various types of medical imaging systems, by way of example, but not as a limitation, X-ray, CT, MRI, positron emission tomography (PET), single-photon emission computed tomography (SPECT), or the like. The materials of the fiducial layer 32 may also be compatible with different combinations of medical imaging systems. The fiducial layer 32 may be designed in such a way that it is easily or readily disposable. Other layers of the sensing patch may be easily reprocessed and reused.

Figure 1:
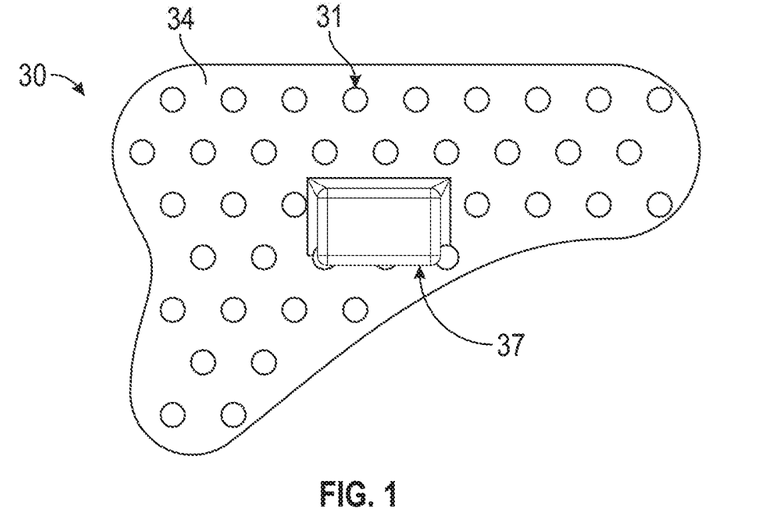
FIG. 1 is a top plan view of a sensing patch according to an embodiment of the present invention.

FIG. 1 depicts the sensor layer 33 along with the control layer 37. These layers may not be compatible with imaging systems and may be removable from the fiducial layer 32 without affecting the attachment of the fiducial layer 32 to the patient's skin.

Figure 6:
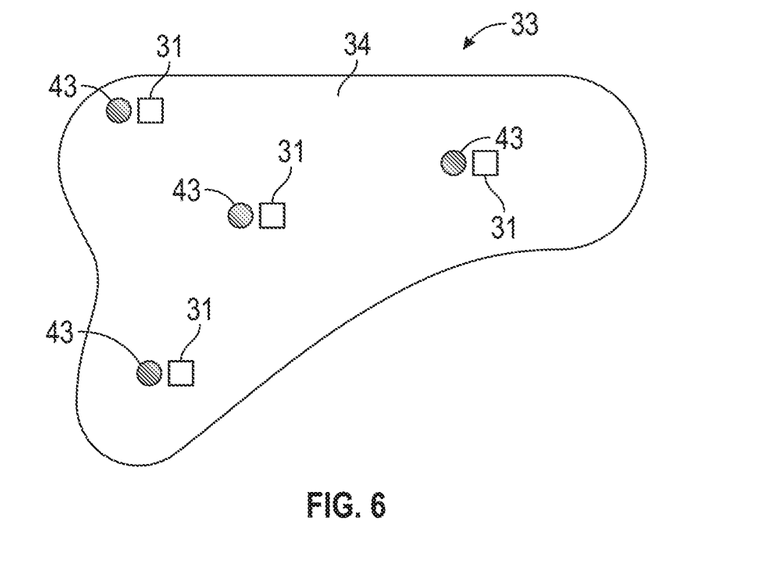
FIG. 6 is a top plan view of a sensor layer of the sensing patch illustrated in FIG. 1.

The sensor layer is depicted alone in FIG. 6. The sensor layer 33 may be comprised of a plurality of sensors 31 forming an array of sensors 31. The sensors 31 may be spaced evenly from one another and disposed on a sensor layer surface 34. The inventive system may consist of one or more arrays of one or more sensors 31. The sensors 31 may include, but are not limited to, sensors capable of detecting magnetic field changes on the nanotesla (nT) scale, voltmeters, or the like. The sensors 31 may be part of a body surface potential measurement system. The sensors 31 may be integrated with or used in combination with an electrocardiograph. Each sensor 31 may have one or more corresponding contact points 43. Each sensor 61 may be placed on or proximate to one or more corresponding contact points 43. At each contact point 43, the sensor 31 may be in electrical communication or direct contact with the patient's skin. Each sensor 31 may acquire patient information at or through its corresponding contact point 43.

Referring now back to FIG. 1, the sensor array may be a grid that includes a plurality of sensors 31 affixed to a sensor layer surface 34. The sensor layer 33 may include a plurality of conductive areas that allow for the plurality of sensors 31 to traverse through the patch material and maintain electrical connection with the patient's skin. In some embodiments, the electrical connection with the patient's skin may be made through the fiducial layer 32.

Each sensor 31 may have one or more contact points with the patient's skin and measure patient information at the one or more contact points. In some embodiments, the sensor 31 may be provided by a voltmeter, or the like, which may allow for the voltage level at that contact point to be measured. In other embodiments, the sensor 31 may be provided by an electric field sensor, or the like, in which case, the electric field magnitude or direction at that contact point may be measured.

Each sensor 31 may serve as a reference potential for one or more other sensors 31. Each sensor 31 may be separated by one or more resistive elements to produce a measurable voltage differential between the sensors 31. The voltage values of specific locations in the patient's body may then be determined through mathematical operations.

The sensor layer 33 portion of the inventive system may further include a specially configured grid of sensors 31. The sensors 31 may include resistor components and voltmeters. Additionally, desired bioinstrumentation amplifier elements, or any such other components necessary to condition the signals being harvested, may be disposed on the sensor layer. These conditioning components may also be located in a control layer 37 affixed to the sensor layer 33 or the fiducial layer.

Referring now again to FIG. 2, the sensor layer 33 may be attached to the side of the fiducial layer 32 that is distal from the patient's skin. The sensor layer 33 may carry the components intended to harvest the electrical signals found on the surface of the patient's skin. The electrode or sensor elements that are contained in the sensor layer 33 may have contact points that are configured to be in direct contact with a patient's skin or may be in direct contact with some conductive element that may improve signal detection capability and itself be in direct contact with the patient's skin.

The conductive element may be contained in the sensor layer 33 and have direct contact with the patient's skin through one or more openings in the fiducial layer 32. In some embodiments, the conductive element may be contained in the fiducial layer 32 and have direct contact with the patient's skin due to the adherence of the sensing patch 30 to the patient's skin.

This sensor layer 33 may comprise a network of resistive elements, wires, printed circuitry, a plurality of voltage potential measurement components, a plurality of magnetic field detection elements, or the like. Bioinstrumentation systems may be contained by the sensor layer 33 or control layer 37 as necessary to produce usable results. Terminals may be contained in the sensor layer 33 and configured to allow for numerous voltage samples to be taken using the sensors 31. Utilizing the measurements of voltage levels at a plurality of contact points, potentials across a plurality of contact points may be calculated. These values may be used to create an electric field map of the patient.

The magnetic field produced by the heart has been measured at approximately 12 nT. Most standard sensors are unable to detect changes in a magnetic field of such small magnitude; however, some potential options do exist. Available sensors may be capable of detecting both field magnitude and field direction in three dimensions, but the sensitivities of these devices may be low. Signal conditioning or noise reduction may be performed on the data acquired by the sensors 31. This post processing may be performed by a control module 37. Electromagnetic field (EMF) shielding may be incorporated in the design of the sensing patch to reduce noise collected by the sensors.

Additionally, micro-magnetic sensors capable of unidirectionally detecting magnetic fields of less than 1 nT in magnitude may be available. Utilizing micro-magnetic sensors may reduce the electronics contained in the control layer 37 or eliminate the need for a control layer 37.

Figure 4:
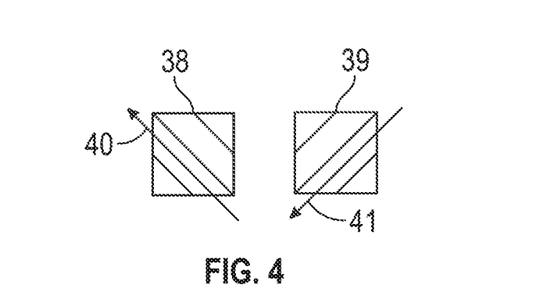
FIG. 4 depicts field sensing directions of the high-sensitivity unidirectional field sensors illustrated in FIG. 3.

By utilizing varying orientations of high-sensitivity unidirectional field sensors, the system may detect different field magnitudes spatially. Field vectors may be established mathematically once the field magnitudes have been measured by sensors of varying orientation. FIG. 4 depicts two high-sensitivity unidirectional field sensors 38 and 39. The resolution of the inventive system, especially in terms of direction, may be entirely dependent upon the number of sensors 38, 39 used. In one embodiment, one stack of two unidirectional sensors 38, 39 may be placed in such a manner that their respective sensing directions are orthogonal to one another. Such a configuration allows for the computation of the sensed magnetic field direction and magnitude. The respective sensing directions of sensors 38 and 39 are shown by arrows 40 and 41.

Figure 3:
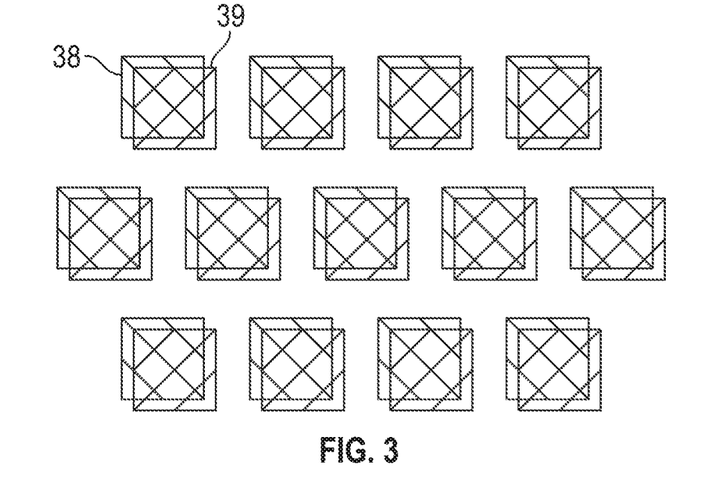
FIG. 3 is perspective view of an array of high-sensitivity unidirectional field sensors to be used in connection with the sensing patch according to an embodiment of the present invention.

The system depicted in FIG. 3 incorporates an array of high-sensitivity unidirectional field sensors 38 and 39. The sensors 38 and 39 may be stacked in pairs with sensing directions orthogonal to one another. These pairs may then be arranged in an array, grid, or other configuration.

A simplified example of the necessary mathematics to determine field strength and direction in two dimensions is shown below.

$$\phi_{B_0} = \tan^{-1}\left(\frac{B_{meas_2}}{B_{meas_1}}\right)$$

$$|B_0| = \sqrt{B_{meas_1} + B_{meas_2}}$$

$\emptyset$=Angle between $B_0$ vector and vertical axis
$B_{meas_1}$=Magnitude detected by sensor oriented vertically
$B_{meas_2}$=Magnitude detected by sensor oriented horizontally
$|B_0|$=Magnitude of $B_0$ vector Returning to FIG. 2, the sensor layer 33 may carry the necessary components to detect nano-scale magnetic fields. These components may be oriented in such a way that the magnitude and directional orientation of the field can be quantified. With the orientation of each individual sensor 31 known and the output voltage resulting from the affecting fields, vector mathematics can be performed to determine these characteristics.

In one embodiment, a change in magnetic field may be detected by one or more sensor 31, which may be caused by the presence of an abnormal amount of or increase in fluid located around the heart. The detection of a changed magnetic field may be indicative of congestive heart failure. The electrical field response may change due to the increase of the dielectric change created by fluid increase. This change can be measured by calculating a difference between one or more of the sensors 31. Calculating and graphically depicting differences in magnetic field between one or more sensors 31 of the sensor layer 33 may create a map of the amount of fluid at different locations around the heart. Similarly, impedance changes may be detected by one or more of the sensors 31 to detect and represent fluid located around the heart.

In one embodiment, the sensors 31 may include an array of magnets 45 adapted to map the location of a foci. The magnets 45 may be used in combination with electric field sensors 44 and a cardiac monitor 46 to detect and locate one or more foci. This may advantageously improve the effectiveness of ablation.

Figure 9:
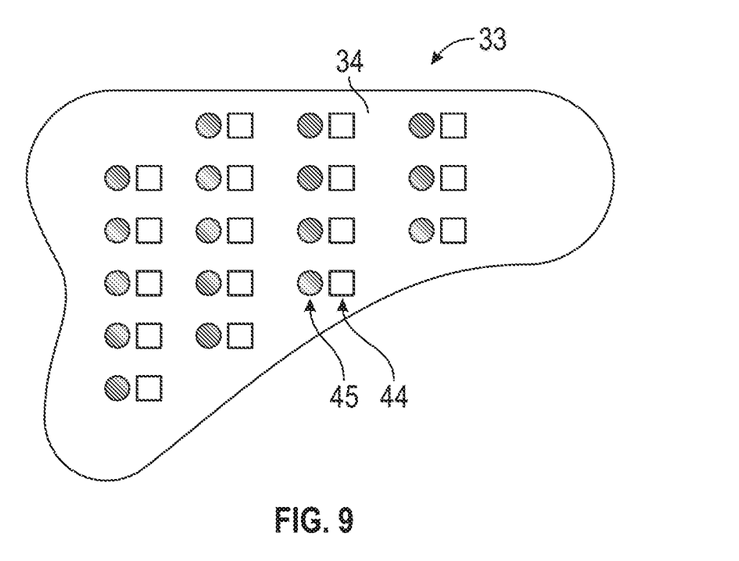
FIG. 9 is a top plan view of a sensor layer of the sensing patch illustrated in FIG. 1, having a lattice of detection.
Figure 10:
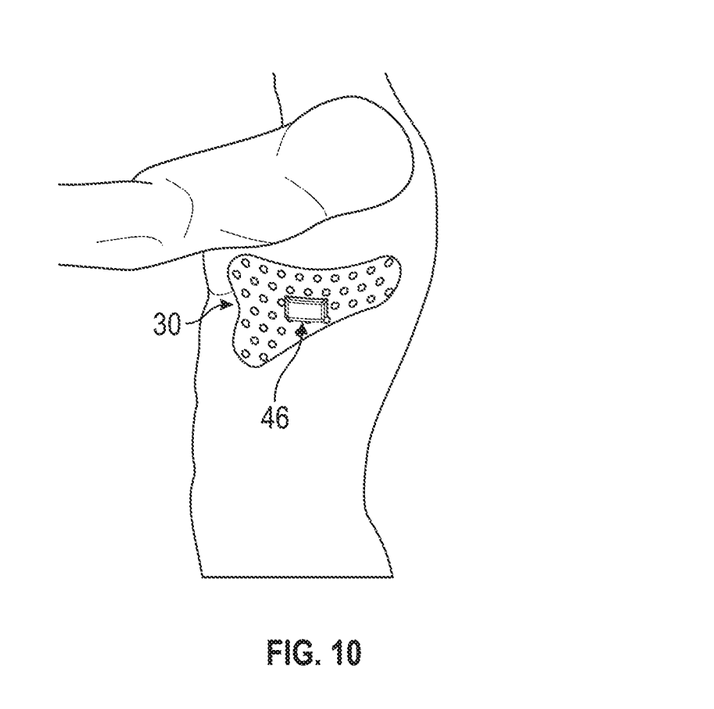
FIG. 10 is an environmental view of the sensing patch illustrated in FIG. 1 affixed to a patient.

As shown in FIG. 9, the array of magnets 45 may be arranged to create a lattice of detection. Each one of the magnets 45 may be associated with a sensor 44 that measures electric field and outputs an electrical signal indicative of the value of the electric field. The output signals from each of the sensors 44 may be combined by the system to create a three-dimensional image of the detected electrical field. This image may be used to locate the foci on the heart.

There may be a known spatial relationship between each sensor 44 or magnet 45 and the fiducial markers 35 secured to a patient. Using this known relationship, the three-dimensional model of the electrical activity of the heart may be correlated to the anatomy of a patient and the location of one or more foci in the heart may be determined.

A cardiac monitor 46, which may be carried by the sensing patch 30, may be used in combination with the sensing patch 30. The cardiac monitor 46 may receive ECG data from one or more electrodes, which may be integrated in an electrode layer of the sensing patch 30. The cardiac monitor may analyze the ECG data to detect and identify atrial fibrillation. The sensors 44 may collect electric field data during the occurrence of atrial fibrillation. That data may be evaluated by the cardiac monitor 46 or an external computing device to locate one or more foci.

In one embodiment, two arrays of magnets 45 may be secured to a patient's body. The two arrays of magnets 45 may be positioned to oppose one another and increase ability of the electric field sensors 44 to locate the foci in three-dimensional space.

A protective layer may comprise protective or shielding elements to improve the accuracy of the electronics or protect the other components of the sensing patch 30. The protective layer may also incorporate or comprise an outer covering to enhance wearer comfort and reduce device interference with daily activities. The protective layer may be placed above the sensor layer or the control layer. The protective layer may encapsulate, surround, or protect any component of the sensing patch.

The sensing patch 30 described here may be used in a system in which a plurality of sensing patches 30 are used in combination with one another in different locations on the body. By way of example, and not as a limitation, a first sensing patch 30 may be placed anterior while a second sensing patch 30 is placed posterior. In another embodiment, two sensing patches may be placed anterior.

The sensing patch 30 may also be implemented as a vest system. In such an embodiment, one or more layers of the sensing patch 30 may be incorporated into a vest. The fiducial layer may adhere to the patient's skin. The sensor layer or control layer may be incorporated into a vest and secured to the fiducial layer to maintain a constant physical relationship between the sensor layer and the fiducial layer.

In another embodiment, a single large patch may cover a large amount of surface area on the body. By way of example, and not as a limitation, a sensing patch 30 may wrap around from anterior to posterior aspects of the torso. In some embodiments, the sensing patch may encompass one or more lateral aspects.

With the integration of properly compatible fiducial markers, the patch system may be integrated with current medical imaging systems and related applications. The fiducial layer 32 of the sensing patch 30 may be removable from the other layers of the device. The method of removal should allow for the fiducial layer 32 to remain in the same position on the patient's skin. The fiducial layer 32, which contains the fiducial markers 35, should remain affixed to the patient's skin during any medical imaging procedure that is performed. The fiducial markers 35 will be visible on the resulting images, which allows the data gathered from the sensors 31 to be accurately correlated with the patient's anatomical character through reference distances, or the like.

Not only does this implementation allow for the imposition of mathematical constraints on the spatial localization of different electro-cardiac structures based on patient anatomy, it also allows for ease of transition from the diagnostic phase to the surgical operating phase. The fiducial layer may remain on the patient during surgery, and may be used to provide image-based, or like, guidance of a catheter or other surgical instrument. The system may also utilize data collected from the sensors or other patch components to target problematic areas.

The mathematical and computational operations necessary to develop a system capable of locating one or more electromagnetic field sources are highly involved. Although the inventive system will provide more constraints on the potential solution to the mapping problems inherent in measuring patent electric and magnetic fields, probabilistic models may also be incorporated to develop a solution. Additionally, the solution may require the ability to isolate and produce models with different numbers of sources.

Electric fields and magnetic fields are affected differently by the various structures in the body. Therefore, they provide data independent from one another. Incorporation of electrical and magnetic sensor arrays in a system such as this is not redundant. Each type of sensor will impose different constraints and yield different possible solutions. The integration of imaging data allows for the system to constrain its solution still further to a certain spatial area defined by the image and correlated to the data by the fiducial markers. The use of ECG data may allow for temporal analysis.

Each group of data will provide its own set of solutions or constraints when attempting to calculate or otherwise determine the location of the problematic field source (cardiac foci, or the like). By combining the data and analyzing them as whole, the number of constraints increases and the number of possible solutions decreases, allowing for more accurate predictions of where the source in question may be located.

In one embodiment, the peak voltage from a node, which may be, but is not limited to, the sinoatrial or atrioventricular node, may be utilized as a reference to normalize all measurements from associated foci. In such an embodiment, one or more sensors may measure an electrical characteristic of the reference node. The measured electrical characteristic may be, but is not limited to, voltage, current, or the like. This measured value of the electrical characteristic may serve as the reference level. The amplitude of the electrical characteristics of associated foci may be measured by one or more sensors and compared to the reference electrical characteristic amplitude to identify or locate foci, which may be affecting AF. The measured electrical characteristic amplitude of foci may be compared to the reference electrical characteristic amplitude to determine the location of each foci using XYZ coordinates from the reference node and measured foci.

In order to obtain more clear and useful data, high sampling frequencies may be used in each system so as to reduce the impact of noise. The high sampling frequencies may help to account for spatial resolution limitations inherent to any system and may allow for spatial localization of sources with higher levels of confidence. For some applications, a type of selective sampling may be used and may be dependent on the intended application. By way of example, and not as a limitation, when attempting to capture data specifically relevant to atrial fibrillation and the source foci, data may be compared to the corresponding ECG traces and all segments preceding the R-peak may be analyzed. Any one of these segments containing a normal, rhythmic P-wave may be ignored, whereas those segments where either no P-wave or an abnormal P-wave morphology is observed may be recorded and processed. This may help to isolate data specific to the problematic foci and eliminate data that will be of no use.

One or more of the leads used to measure and map these body surface potentials may also double as ECG leads to provide ECG data. Provided there are a sufficient number of suitable leads, multiple ECG channels may be measured.

The incorporation of built-in fiducial markers 35 on the fiducial layer 32, which are compatible with different clinically used medical imaging systems, allows for data collected by the sensors 31, or otherwise by the inventive device, to be accurately cross-referenced with high-resolution anatomical images of the patient. This ability may be useful in both standard imaging procedures as well as in applications involving real-time image-guided surgery, where continuous scanning (generally CT) takes place as visual aid for the surgeon. Fiducial markers 35 may be used as a reference to aid in various medical or surgical procedures, such as catheter-based guidance or mapping. Data provided by the medical images containing fiducial marker 35 references may be used to impress more mathematical constraints on the calculations to locate different electric field and magnetic field sources within the patient.

Many smaller facilities lack the equipment necessary to perform in-house medical imaging procedures like CT or MRI scans. For this reason, the inventive system may be capable of performing similar operations with ultrasound imaging modality (US). US systems utilize the acoustic properties of tissue to form medical images and require that the probe be in contact with the patient to perform the scan. Therefore, the incorporation of fiducial markers 35 in a US application may require a different approach than in the other modalities. In known systems, fiducial markers 35 may work in a passive manner to correlate the US images to fiducial markers only when the fiducial marker 35 is placed invasively within the patient's body. A standard, relatively large superficially placed fiducial marker may not be of any use, or may be of only limited use, for spatial reference in the US system because the majority of data collected by the US system comes from within the body. At least two potential solutions to this problem are included within the inventive concept.

In one solution, the sensing patch 30 may comprise one or more active or semi-active fiducial markers 35 that may be capable of communication with a US probe. Such a configuration utilizing active or semi-active fiducial markers 35 may allow the system to localize where the US probe is with respect to one or more fiducial markers 35 disposed on the sensing patch 30. This information may allow for correlation with the other data collected by, for example, the sensors 31. Several possibilities exist to produce a system containing active or semi-active fiducial markers 35. One possible embodiment may include incorporation of RF or IR communication in one or more of the fiducial markers 35 or US probe. In some embodiments, a device may be attached to the US probe, and a process for calibration may be followed prior to, during, or subsequent to one or more US procedures. A US system incorporating active or semi-active fiducial markers 35 may have no, or only limited, adverse effects on the US image due to fiducial interference, or the like. In many 3D US systems, this type of communication between the probe and the computer system already exists; however, selecting this design could limit potential users to those who have relatively more expensive US systems. The inventive system may include adaptive hardware to upgrade existing US systems to utilize the inventive systems and methods.

Another embodiment of a potential solution involves the use of a sheet of very small, but detectable, superficial fiducial markers 35. A layer of the sensing patch 30 that contacts the patient's skin, the fiducial layer 32, may comprise an organized pattern of small fiducial markers 35, which may be depicted in a US image when the beam of the US probe is directed through the fiducial markers 35.

In such an embodiment, the fiducial layer 32 may be constructed from a material that has acoustic properties similar to human tissue. Additionally, the fiducial markers 35 may be designed or oriented in such a way that the US image of the target area is not substantially affected by the presence of the fiducial markers 35. By incorporating a variety of unique fiducials within the sensing patch 30, US data can be correlated spatially to the sensing patch 30 with a theoretically high degree of accuracy even if the sensor layer 33 is removed from the sensing patch 30. The US probe may need to rapidly alternate between high and low frequency transmission bands in order to simultaneously detect the superficial fiducial markers 35 and the anatomical structures deeper within the body. Frequencies between 10 and 15 MHz may be necessary to image the fiducial markers 35 while a frequency less than 7 MHz may be necessary to image the anatomical structures within the body. Such an embodiment may also provide the added benefits of non-invasive, passive markers, and no extra hardware required to localize the probe itself.

Embodiments of the inventive device and methods may require software to interpret the data and reconstruct accurate images which correlate with the sensor 31 data according to the fiducial markers 35. Benefits from both systems may be experienced in either 2D or 3D US systems.

Returning to FIG. 1, the spatial resolution of the inventive mapping system may be directly dependent upon the number of sensors 31, and corresponding contact points, within the array. A plurality of sensors 31 may comprise a voltmeter. The number of sensors 31 may be determined by the number of voltmeters that may be implemented in the system. The spacing of the contact point or points associated with each sensor may be a tunable value. However, it may be beneficial to maintain constant spacing between each contact point. The voltage measurement taken by each sensor 31 at its corresponding contact point may be correlated spatially to other measurements using the relevant formulated equation associated with each contact point. This information may then be used to produce a surface map of the body surface potentials of the patient within the range of the device. A plurality of samples of the measured voltage levels or electric field may be taken over a period of time, using an appropriate sampling frequency, to produce a time-varying map of the body surface potentials (isochrones).

Returning to FIG. 1, some contact points used by the sensors 31 of the system described above could potentially double as contact points for electrodes to gather electrocardiograph (ECG) signals. The contact points chosen from the inventive mapping system to provide information to an ECG may be organizationally consistent with standard ECG electrode layouts used in a clinical setting. By measuring the ECG signals, data acquired from the sensors 31 or through other systems may be compared isotemporally against known cardiac cycle information. For example, the data acquired at a given time by the inventive sensor system may be matched with its concurrent ECG signal. This would allow for the data acquired by the sensors 31 during atrial contraction to be isolated and processed through the identification of P-wave initiation in the ECG signal trace. The same holds true for any other system used in the inventive device or method, and for any stage of the cardiac cycle.

A voltmeter separate from the sensors 31 may be implemented to measure the potentials across the contact points that may be utilized to produce the desired channel of ECG signal. Similarly, data from the sensors 31 may be used to calculate the potentials across those contact points providing ECG data. Such an implementation may reduce the hardware requirements of the system. The total extent of the potential applications of this technology is unknown; however, the main foreseeable impact of this technology would be in the realm of cardiology, both in diagnostic and surgical areas. Current methods may take several hours of invasive surgery just for the identification of problematic areas. Non-invasive identification and spatial localization of problematic electrocardiac components would save patients and doctors considerable time currently spent in surgery to identify these things. Essentially, this system can use image-based guidance provided by the fiducial markers to guide the surgeon to the area which has been identified as problematic by the sensor systems, which at the very least would provide potential areas of where the problem(s) are located with high probability, if not with certainty.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the description of the invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

That which is claimed is:

1. A system for cardiac monitoring comprising:
   a patch comprising:
      a sensor layer comprising:
         an array of first sensors, each of the first sensors is adapted to measure a value of magnetic field in a first direction,
         an array of second sensors, each adapted to measure a value of the magnetic field in a second direction, which is orthogonal to the first direction, and
         an array of magnets, wherein each of the array of magnets is collocated and associated with one of the array of first sensors and the magnetic field measured by each of the first sensors is the magnetic field of a respective magnet from the array of magnets associated with its respective first sensor, and
      adhesive disposed along an outer surface of the sensor layer; and
   a cardiac monitor adapted to detect atrial fibrillation, receive outputs of each of the array of first sensors and each of the array of second sensors during the atrial fibrillation, wherein the output is an electrical signal indicative of the respective value of the magnetic field at the respective sensor's location during the atrial fibrillation, and provide the outputs of each of the arrays of first and second sensors to an external computing device; and
   the external computing device adapted to receive the outputs of each of the arrays of first and second sensors and utilize the respective value of the magnetic field at the respective sensor's location during the atrial fibrillation to locate a foci causing the atrial fibrillation.

2. The system according to claim 1 wherein the sensor layer is adapted to adhere to a patient and wrap from an anterior to a posterial aspect of a torso of the patient.

3. The system according to claim 1 further comprising:
   a fiducial layer having a surface adapted to secure to the sensor layer, wherein the fiducial layer further comprises:
      a plurality of fiducial markers having at least one of acoustic properties, material density, and proton content different from those of human tissue.

4. The system according to claim 1 further comprising:
   an electrode layer having at least one electrode and secured to the sensor layer; and
   wherein the cardiac monitor is in electrical communication with the at least one electrode.

5. The system according to claim 4 wherein the cardiac monitor is adapted to identify the atrial fibrillation in data provided by the at least one electrode.

6. The system according to claim 1 wherein the external computing device provides a three-dimensional image indicating the location of the foci on a heart.

7. A system for cardiac monitoring comprising:
   a patch comprising:
      a sensor layer comprising:
         an array of first sensors, wherein each of the first sensors is adapted to measure a value of a magnetic field in a first direction,
         an array of second sensors, each adapted to measure a value of the magnetic field in a second direction, which is orthogonal to the first direction, and
         an array of magnets, wherein each of the array of magnets is collocated and associated with one of the array of first sensors and the magnetic field measured by each of the first sensors is the magnetic field of a respective magnet from the array of magnets associated with its respective first sensor;
      adhesive disposed along an outer surface of the sensor layer,
      a fiducial layer having a surface adapted to secure to the sensor layer, and
      an electrode layer having at least one electrode and secured to the sensor layer;
   a cardiac monitor adapted to detect atrial fibrillation, receive outputs of each of the array of first sensors and each of the array of second sensors during the atrial fibrillation, wherein the output is an electrical signal indicative of the respective value of the magnetic field at the respective sensor's location during the atrial fibrillation, and provide the outputs of each of the arrays of first and second sensors to an external computing device; and
   the external computing device adapted to receive the outputs of each of the arrays of first and second sensors and utilize the respective value of the magnetic field at the respective sensor's location during the atrial fibrillation to locate a foci causing the atrial fibrillation;
   wherein the sensor layer is adapted to adhere to a patient and wrap from an anterior to a posterial aspect of a torso of the patient;
   wherein the fiducial layer comprises a plurality of fiducial markers having at least one of acoustic properties, material density, and proton content different from those of human tissue;
   wherein the cardiac monitor is in electrical communication with the at least one electrode; and
   wherein the cardiac monitor is adapted to identify the atrial fibrillation in data provided by the at least one electrode.

8. A system for cardiac monitoring comprising:
an array of first sensors, each of the first sensors is adapted to measure a value of magnetic field in a first direction;
an array of second sensors, each adapted to measure a value of the magnetic field in a second direction, which is orthogonal to the first direction;
an array of magnets, wherein each of the array of magnets is collocated and associated with one of the array of first sensors and the magnetic field measured by each of the first sensors is the magnetic field of a respective magnet from the array of magnets associated with its respective first sensor; and
a cardiac monitor adapted to detect atrial fibrillation, receive outputs of each of the array of first sensors and each of the array of second sensors during the the atrial fibrillation, wherein the output is an electrical signal indicative of the value of the magnetic field at the respective sensor's location during the atrial fibrillation, and provide the outputs of each of the arrays of first and second sensors to an external computing device; and
the external computing device adapted to receive the outputs of each of the arrays of first and second sensors and utilize the respective value of the magnetic field at the respective sensor's location during the atrial fibrillation to locate a foci causing the atrial fibrillation; and
wherein adhesive is disposed along an outer surface of the sensor layer.

* * * * *